(12) United States Patent
Khanuja et al.

(10) Patent No.: US 6,423,741 B1
(45) Date of Patent: *Jul. 23, 2002

(54) ANTI-MICROBIAL COMPOSITION AND METHOD FOR PRODUCING THE SAME

(75) Inventors: Suman Preet Singh Khanuja; Suchi Srivastava; Tiruppadiripuliyur Ranganathan Santha Kumar; Ajit Kumar Shasany; Dharam Chand Jain; Mahendra Pandurang Darokar; Dharmendra Saikia; Sushil Kumar, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 09/538,439

(22) Filed: Mar. 29, 2000

Related U.S. Application Data

(63) Continuation-in-part of application No. 09/179,204, filed on Oct. 27, 1998, now Pat. No. 6,127,405.

(30) Foreign Application Priority Data

Jul. 10, 1998 (IN) .................................... 1967/DEL/98

(51) Int. Cl.$^7$ ..................... A61K 31/335; A61K 31/47
(52) U.S. Cl. ..................... 514/450; 514/311; 514/312; 514/314
(58) Field of Search .................... 514/450, 311, 514/312, 314

(56) References Cited

U.S. PATENT DOCUMENTS

| 4,973,590 A | * 11/1990 | Preiss et al. ............. 514/254 |
| 5,057,501 A | * 10/1991 | Thornfeldt ................ 514/53 |
| 6,127,405 A | * 10/2000 | Kumar et al. ............. 514/450 |

* cited by examiner

*Primary Examiner*—Kevin E. Weddington
(74) *Attorney, Agent, or Firm*—Ladas & Parry

(57) ABSTRACT

This invention is related to the development of strategic and novel composition comprising α arteether and nalidixic acid or quinolone drugs, said composition useful as an advanced generation drug to counter the resistance development itself and having a potential to be used in treating infectious diseases and in inhibiting the resistance developed due to mutation in the gyr A gene of bacteria, particularly in those cases where drug resistant strains are known to appear very frequently.

28 Claims, 1 Drawing Sheet

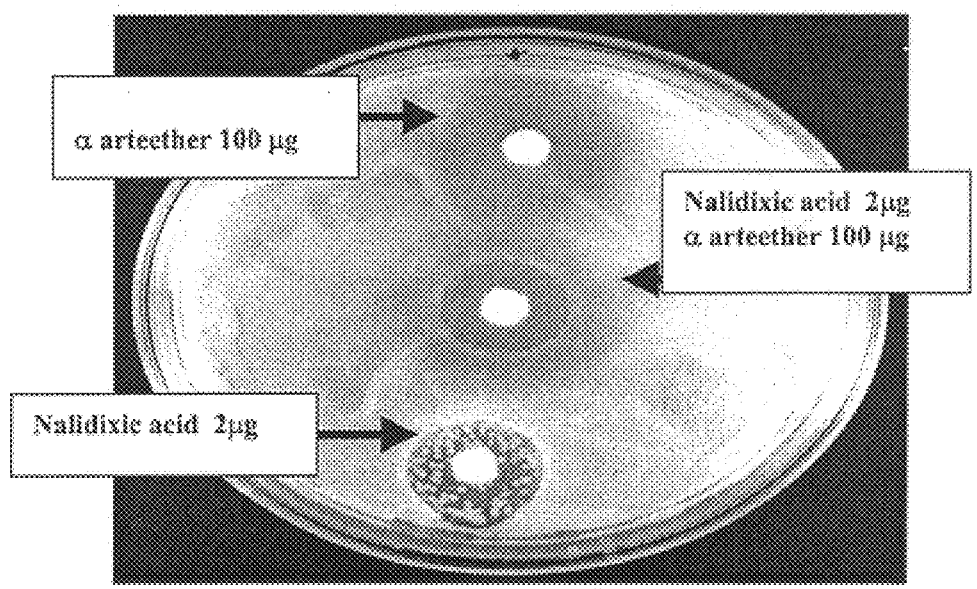

ANTI-MICROBIAL COMPOSITION AND METHOD FOR PRODUCING THE SAME

This application is a continuation-in-part of application Ser. No 09/179,204 filed Oct. 27, 1998, now U.S. Pat. No. 6,127,405.

FIELD

The invention is related to the development of strategic and novel anti-microbial composition comprising a arteether, quinolones and similar drugs, which can be used as an advanced generation drug composition against infections and simultaneously to counter the resistance development in bacteria by an in built mechanism of action to eliminate resistant cells.

BACKGROUND OF INVENTION

Since the discovery of penicillin by Alexander Flemming, the developments in drug discovery have undergone a sea of change. With increased and indiscriminate use of drugs, the infectious agents are tending to become resistant by adopting different means for inactivating the drug molecules which otherwise control them by inhibiting their vital life processes. Out of many inhibitory molecules, only a few are used as drugs because many of them are not safe for human and animal consumption. The pace of drug discovery is thus slower than the evolution of newer resistant strains of infectious agents. This is due to the fact that mutations occur spontaneously in a random manner but due to selection pressure by continued presence/administration of antibiotics, the resistant organisms proliferate unlimitedly circumventing the effect of the drug molecules. To counter this drug resistance menace, the existing drugs proven safe for human consumption with minimal side effects are usually modified chemically for more effectiveness. This has led to the development of first generation, second generation and third generation drugs/antibiotics to counter the parallel evolution of resistance. In addition to modifying the structure, another novel but simple way which has been conceived and developed in the present invention is to administer the drugs in combination i. e. the first generation drugs may be used with other safe compound such that the sensitive bacteria can be killed by the first generation antibiotic and the resistance developed if any can be killed by the second compound and conversely the resistant cells against second compound are killed by first antibiotic due to genetic basis of resistance-sensitivity relationship.

In this invention, the applicants used a unique composition of known compounds with different and specific counter modes of actions to control the resistance menace in bacteria. This invention is novel in terms of the idea of combining two known molecules for not only controlling/killing bacteria but also preventing the appearance of resistant strains due to counter-actions wherein, one molecule kills bacteria resistant to other and vice versa and finally leading to prevention of resistance development itself. This phenomenon of sensitivity of cells to the one upon resistance development against other and vice versa is genetically governed, and hence is a self sustaining process once the right kind of anti-microbial molecules have been identified through study of specific mutations, which was achieved in the invention.

The compounds a and α and β arteethers were synthesized from dihydroartemisinin by etherification with ethanol. These earlier were developed as anti-malarial drugs in India by Central Institute of Medicinal and Aromatic Plants (CIMAP), Lucknow and Central Drug Research Institute (CDRI), Lucknow, India after phase III clinical trial. Absolute stereochemistry of arteethers at C-12 were also determined and found that it is 2–3 times more potent than artemisinin. In U.S. patent application Ser. No. 09/176,204, the Applicants had demonstrated that the compound a arteether can specifically kill certain drug resistant bacteria, hence capable of being used as an antibiotic.

For bacterial growth, DNA gyrase enzyme is essential for being involved in the replication of DNA and hence cell division. This enzyme transiently breaks the DNA strands and introduces negative superhelical turns in an ATP-dependent process. The $E.coli$ DNA gyrase enzyme is a tetramer with two subunits A and B. The subunit A is nalidixic acid sensitive but certain mutation(s) in this subunit makes the bacteria resistant to nalidixic acid. In the said U.S. patent application, the Applicant had shown that normal wild type bacteria are not killed by α arteether but the mutants resistant to nalidixic acid and other fluoroquinolones (with modified gyrase) are highly sensitive to a arteether, whereas the bacteria with normal A subunit are killed by nalidixic acid.

It is also important to note that globally $Mycobacterium$ $tubercztlosis$ infects about ten million people killing about three million each year making this bacteria the greatest cause of mortality by any single infectious agent worldwide. Quinolones and derived fluoroquinolones are a part of the common chemotherapy against tuberculosis. Quinolones have been shown to inhibit DNA gyrase activity such as relaxation of DNA supercoiling during the DNA replication. Several investigators have shown that point mutations in gyrA gene located in a very small region between 0–400 nucleotides of the gyrA gene are responsible for quinolone resistance acquired by different strains of $E.coli$ selected either in-vitro or in-vivo. The resistance mechanisms that have developed due to mutations in gyrA gene in Mycobacteria are related to $E.coli$. The mechanism of quinolone resistance appears fairly similar between $E.coli$, Mycobacteria, $H. influenzae$ and in many other bacteria In the earlier invention, the applicants had found the novel property of the compound α arteether i. e. it is effective against the gyr mutant ($Nal^r$) strains of $E.coli$ but ineffective against wild type ($Nal^s$) strains. So the applicants thought of combining the already out of use quinolone, nalidixic acid with a arteether to generate a composition in preventing resistance development itself Accordingly, the present application is filed as a continuation-in-part of copending U.S. application Ser. No.09/176,204.

It is also important that these compounds and their activity are already known individually (quinolones since 1960 and α arteether since the Applicants US application). But the activity of the combination of these two are not reported till date and Applicants have developed a composition which is cheap, safe, and wherein the already tested antibiotics can be used in tandem with the already tested safe compound α arteether. The results were fully substantiated with the experimentation in this direction. The two molecules in these combinations killing the resistant bacteria against each other will not permit any resistant strains/mutants to proliferate which constitutes the basis of drug resistance development in microbes.

OBJECTS

The main object of the invention is to develop a novel anti-microbial composition comprising a arteether, quinolones and similar drugs.

Another object is to provide a novel anti-microbial composition useful in countering the development of resistance itself Yet another object is to develop an anti-microbial composition capable of killing bacteria resistant to conventional drugs and prevent proliferation of resistant or mutant strains of bacteria.

SUMMARY OF THE INVENTION

This invention is related to the development of strategic and novel composition comprising a arteether, quinolones and similar drugs which can be used as advanced generation drug(s) to counter the resistance development itself while, having a potential to be used in treating infectious diseases particularly in those cases where drug resistant strains are known to appear very frequently. The uniqueness and most useful feature is that, because the composition is a combination of α arteether and quinolone drugs, the spontaneous mutants arising resistant to Quinolones or its derivatives will be killed by α arteether and at the same time any α arteether resistant strains become highly sensitive to nalidixic acid and hence eliminated by it through the combination approach. The new composition inhibits the resistance development due to mutation in the gyr A gene of bacteria, in which one component is α-arteether and the other may be nalidixic acid or any of the fluoroquinolones (comprising Ciprofloxacin, Norfloxacin, Levofloxacin, Sparfloxacin, Oxfloxacin and Lomefloxacin etc.) or compounds of similar nature against which the resistance may develop through a related process.

DETAILED DESCRIPTION

Accordingly, the invention provides fourth generation anti-microbial composition for inhibiting drug resistance, said composition comprising two components, wherein one component is α-arteether and the other component is a drug selected from quinolones, their derivatives or any other similar compound against which the resistance develops.

In an embodiment, the quinolone compound used is but not limited to nalidixic acid.

In still another embodiment, the ratio of α-arteether and quinolones in the composition is about 8:1 to 20:1.

In yet another embodiment, the quinolone derivatives are selected from the group of fluoroquinolones comprising Ciprofloxacin, Norfloxacin, Levofloxacin, Sparfloxacin, Oxfloxacin and Lomefloxacin.

In a further embodiment, the concentration of nalidixic acid is at least 50 µg/ml.

In yet another embodiment, concentration of α-arteether in the composition is about 2mg to 500 mg/ml.

In still another embodiment, the concentration of α-arteether in the composition is about 400 µg/ml.

In another embodiment, concentration of quinolone drugs in the composition is about 0.5 mg to 500 mg.

In another embodiment, the neutralized sterile vegetable oil or a similar solvent is used as a base in an amount of at least 1 ml.

In yet another embodiment, the said components are selected from DNA gyrase inhibitors with counter-action properties against resistant mutants of each other which include α-arteether and quinolone derivatives.

In another embodiment, the said components are selected from DNA gyrase inhibitors with counter-action properties against resistant mutants of the first and a second components i.e. to α-arteether and quinolones, its derivatives or similar compounds.

In still another embodiment, the composition has inhibitory activity on DNA replication in prokaryotes and thus, can be used as a potential fourth generation drug composition.

In a further embodiment, the second component used may be a first generation quinolone drug selected from but not limited to nalidixic acid and oxalinic acid.

In another embodiment, the second component used may be a second generation quinolone drug selected from but not limited to Ciprofloxacin, Norfloxacin, Levofloxacin, Sparfloxacin and Oxfloxacin.

In yet another embodiment, the second component used may be a third generation quinolone drug selected from but not limited to Lomefloxacin, tosufloxacin, temafloxacin.

In another embodiment, the said composition can be used in place of first, second and third generation drugs against resistant as well as sensitive infections.

In still another embodiment, the said composition can be used to prevent the development of resistance against first, second and third generation drugs.

Further, the invention provides a method for the development of fourth generation anti-microbial composition for inhibiting drug resistance, said method comprising the steps of mixing α-arteether and a drug selected from quinolones, their derivatives or any other similar compound against which bacteria develop resistance.

In an embodiment of the method, the ratio of α-arteether and quinolones in the composition is about 8:1 to 20:1.

In another embodiment of the method, the quinolone compound used is but not limited to nalidixic acid.

In a further embodiment of the method, the quinolone derivatives are selected from the group of fluoroquinolones comprising Ciprofloxacin, Norfloxacin, Levofloxacin, Sparfloxacin, Oxfloxacin and Lomefloxacin.

In yet another embodiment of the method, the concentration of nalidixic acid is at least 50 µg/ml.

In yet another embodiment of the method, the concentration of α-arteether in the composition is about 2 µg to 500, µml.

In another embodiment of the method, the concentration of α-arteether in the composition is about 400 µg/ml.

In still another embodiment of the method, concentration of quinolone drugs in the composition is about 0.5 mg to 500 mg.

In an embodiment of the method, neutralized sterile vegetable oil or a similar solvent is used as a base in an amount of at least 1 ml.

To define precisely the invention, the applicants have developed a novel composition or drug system to successful check the resistance development as a result of the mutants arising from nalidixic acid application (or any future resistance that will develop from α arteether if the compounds are applied individually) by treating the bacterial infection with the composition. As those compounds are already tested for their safe level of application in human, it is possible to develop and directly use the combination drug to fight infections and simultaneously check resistance menace.

In other experiments the applicants used different combinations of nalidixic acid and α-arteether .in disk diffusion and broth assays for the mutants of both *Mycobacterium smegmetis* and *E. coli*. In case of each of the single compound applications, emergence of resistant colonies was observed within the halo produced by the poison disks. But in case of the disks containing the combination (comprising of half concentration of each) the halo of killing/inhibition did not show any colonies to emerge even upon a prolonged incubation (FIG. 1). Among various combinations of nalidixic acid (24μg to 500 μg) and α-arteether (20 μg to 2000 μg), the compositions containing nalidixic acid: α-arteether in the ratio of 16:1 was the most active against both the microorganisms. Thus, this combination in 16:1 ratio of nalidixic acid: α-arteether is highly effective in prevention of the resistance development by bacteria against either of the two drug molecules. However, other ratios and combinations also could prevent resistance emergence but at varying levels.

Further, it is worth noting here that the said compounds of the invention are already in use for human consumption and the safety data of applications of the compounds are already known. As a known example of prior art (Asthana, O. P, Srivastava, J. S and Valecha, N., 1997. Current status of the artemisinin derivatives in the treatment of malaria with focus on arteether. Journal of Parasitic Diseases. 21: 1–12.), α/β arteether mixture is given at 150 mg doses (one dose per day, for 3 days) as intramuscular injection for treatment of drug resistant and cerebral malaria cases. The injections in the mentioned preparation are prepared in neutralized vegetable oil. Both the compounds of invention that is, α arteether and the quinolones have shown the best activities at pH 7.0 (neutral) in our experiments. Thus, the composition of this invention can be used to treat bacterial infections, particularly the cases where the emergence of drug resistance is known to have high incidence level. The said composition/composition can be employed for prevention of resistance development through random mutations occurring in bacteria against antibiotics. Various classes of quinolone drugs thus can be administered along with α-arteether in form of injection by suspending the compound in the neutralised vegetable oil. Quinolone drugs in the composition can be administered in variable doses ranging from 0.5 mg to 500 mg.

Composition
1. α-arteether (2 mg to 500 mg)
2. Quinolone drugs (0.5 mg to 500 mg)
3. Neutralised sterile vegetable oil at least 1ml Quinolone drugs comprise of Nalidixic acid, Ciprofloxacin, Norfloxacin, Levofloxacin, Sparfloxacin, Oxfloxacin and Lomefloxacin etc.

Thus, the invention provides a new composition of antimicrobial compounds inhibiting the resistance development due to mutation in the gyr A gene of bacteria, in which one component is α-arteether and the other may be nalidixic acid or fluoroquinolones (comprising of Ciprofloxacin, Norfloxacin, Levofloxacin, Sparfloxacin, Oxfloxacin and Lomefloxacin etc.) or compounds of similar nature against which the resistance develops.

In another embodiment of the invention the components of the novel composition are but not limited to α-arteether and nalidixic acid.

Yet another embodiment of the invention provides a composition wherein the compounds have the inhibitory activity on DNA replication in prokaryotes and thus can be used as a potential advanced generation drug composition.

In the other embodiment of the invention the components of the compositions could be DNA gyrase inhibitors with counter-action properties against mutants developing resistance to any one of the two drugs of the combination, which include α-arteether and quinolone derivatives.

In the yet another embodiment the invention provides a new composition wherein the components of the compositions could be α-arteether (2mg to 500 mg), quinolone drugs (0.5 mg to 500 mg) and neutralized sterile vegetable oil at least 1ml.

BRIEF DESCRIPTION OF THE
ACCOMPANYING DRAWING:

The invention is further illustrated with reference to the accompanying drawing which shows a poison disk assay of the composition of the invention against the mutants in *e. coli*. 1 represents the poison disk assay of the composition of the invention against the mutants in *E.coli*.

The following experiments shown as examples of the invention to illustrate some of the embodiments of the invention and should not be construed to limit the scope of the invention in any manner. These experiments were critically performed to use the counteractive properties of quinolones, like nalidixic acid and a arteether against mutant strains resistant to each other and determining the efficiency in controlling the bacteria and preventing the resistance development.

EXAMPLE 1

Monitoring Emergence of Nalr Mutants.

In an experiment, the applicants first determined the frequency of spontaneous mutations in the bacteria *Escherchia coil* (Kumar, S. 1976. *Journal of Bacteriology*, 125: 545–555.) and *Mycobacterium smegmatis* (Snapper, S. B., Melton, R. E., Mustafa, S., Kieser, T. and Jacobs, W. R. 1990. *Molecular Microbiology*. 4:1911–1919.) leading to subsequent resistance development through selection in the presence of these drugs. Known titers of broth cultures of the bacteria were diluted and plated on poison agar medium containing 50 μg/ml nalidixic acid, and the resistant colonies thus developed were counted to estimate the frequency of drug resistance (Nal) development (Table 1).

TABLE 1

Frequency of spontaneous resistance developed against Nalidixic acid.

| Bacteria | Frequency |
|---|---|
| *Escherchia coli* (Wild type) | $7.1 \times 10^{-9}$ |
| *Mycobacterium smegmatis* (Wild type) | $1.0 \times 10^{-10}$ |

EXAMPLE 2
Monitoring Emergence of α-arteether$^r$ mutants.

Further to determine the frequency of spontaneous resistant mutants in *Escherchia coil* and *Mycobacterium smegmatis* for α-arteether, the applicants used the nalidixic acid resistant mutants from the earlier example as the wild type strains since those were sensitive to α-arteether to isolate α-arteether resistant colonies. Known titers of broth cultures of the mutant (Nal) bacteria were diluted and plated in petriplates containing 1000 μg/ml α-arteether, and the resistant colonies thus developed were counted to determine the frequencies (Table 2).

TABLE 2

Frequency of spontaneous resistance developed against α-arteether.

| Bacteria | Frequency |
|---|---|
| *Escherchia coli* (Nal$^r$) | $1.8 \times 10^{-9}$ |
| *Mycobacterium smegmatis* (Nal$^r$) | $1.1 \times 10^{-10}$ |

EXAMPLE 3
Counter-action Study of Nalidixic Acid and α-arteether in Combination Against Resistant Mutants of Each Other.

Upon plating the broth cultures on combination poison agar, no resistant colonies were detected for either of the resistant mutants i. e. for nalidixic acid and α-arteether separately or together, when grown in presence of 50 μg/ml Nalidixic acid and 1000 μ/α-arteether.

Since pathogens always try to counter the drug by genetically modifying itself through mutation(s) in the region of the drug target gene, it is necessary to kill those mutant(s) resistant cells for effective drug management. With this rationale, the applicants evaluated a selected drug resistant mutant strain (Ml) for nalidixic acid (wild type strains being sensitive to nalidixic acid). This mutant strain developed from wild type was defective in Gyr A subunit confirmed by mobilizing a plasmid bearing a wild type gyr A gene. Interestingly the gyr A$^-$ mutant developed from the wild type was sensitive to the compound αarteether but resistant to nalidixic acid. Similarly a second mutant (M2) developed from the gyr A$^-$ mutant strain (Nal$^r$) became sensitive to nalidixic acid which being resistant to α arteether (Table 3). It was noted that invariably among all the tested strains, those resistant to nalidixic acid were sensitive to α arteether and the strains sensitive to nalidixic acid were resistant to cc arteether. A combination of these drugs where both the components are combined together, the question of resistance development does not arise. This is so, because the resistance to nalidixic acid is developed by gyr A mutation and the mutants will be killed by α arteether while, the α-arteether resistant strains will automatically become nalidixic acid sensitive and thus will be killed by nalidixic acid and this way all the spontaneous resistant bacteria could be contained.

TABLE 3

Sensitivity of *E. coli* strains to nalidixic acid and α arteether.

| Bacterial strain | Sensitivity to Nalidixic acid | | | Sensitivity to α arteether | |
|---|---|---|---|---|---|
| | 10 μg/disc | 20 μg/disc | 50 μg/disc | 400 μg/disc | 800 μg/disc |
| *E. coli* (Wildtype) | S | S | S | R | R |
| M1 (Mutant) | R | R | R | S | S |
| M2 (Mutant) | S | S | S | R | R |

EXAMPLE 4
Correlation Between Levels of Counter Resistance and Sensitivity

To determine the correlation between nalidixic acid and α-arteether sensitivity, the applicants selected *Escherchia coli* cultures which were resistant to nalidixic acid at varying degrees (concentrations). Based on the minimal inhibitory concentration of nalidixic acid, *Escherchia coli* mutants were grouped as highly sensitive (MIC less than or equal to 10 μg/ml), resistant (MIC 10 to 200 μg/ml), highly resistant sensitive (MIC more than or equal to 200 μg/ml). These strains were then tested for their sensitivity against α-arteether by estimating their growth (Absorbance at 620 nano meter wavelength of light) in presence of increasing concentrations of α-arteether. The absorbance data was converted to percent growth by considering the absorbance in control as 100%. The growth was then quantified as follows: 1.) greater than 80% growth : the mutant is highly resistant to α-arteether; 2.) 20 to 80% growth : the mutant is moderately resistant to α-arteether; 3.) less than 20% growth : the mutant is sensitive to α-arteether. The experimental data demonstrates that the *Escherchia coli* mutants that are highly resistant to nalidixic acid are on the other hand highly sensitive to α-arteether. In other words *Escherchia coli* mutants most resistant to nalidixic acid are most efficiently killed by α-arteether (Table 4) and vice versa.

TABLE 4

Correlation between the levels of counter resistance and sensitivity

| Bacterial mutants | Minimum inhibitory concentration of nalidixic acid (μg/ml) | Growth at increasing concentrations of α-arteether (μg/ml) | | | |
|---|---|---|---|---|---|
| | | 400 | 800 | 1200 | control |
| A1 | Less than 4.0 (highly sensitive) | 0.858 (93%) | 0.854 (93%) | 0.817 (89%) | 0.921 (100%) |
| A2 | 37.5 (resistant) | 0.607 (66%) | 0.539 (58%) | 0.458 (50%) | 0.917 (100%) |
| A3 | 150.0 (resistant) | 0.421 (50%) | 0.405 (47%) | 0.390 46% | 0.846 (100%) |
| A4 | Greater than 300.0 (highly resistant) | 0.017 (2%) | 0.007 (0.7%) | 0.000 (0%) | 0.961 (100%) |

EXAMPLE 5
Evaluating the Development of Resistant Strains Against the Combination by Co-culturing of Counter Resistant Strains.

Continuing with the experimentation the applicants analyzed the growth of the mutant strains individually and upon co-cultivation compared to the wild type in presence of the compounds individually and in combination. As evident from Table 5, individually the mutants are either sensitive to nalidixic acid or a arteether separately but when treated with the combination of both the compounds no growth was observed either in the individual mutant strains or the mixture of mutants demonstrating no double or single resistance development in the strains whether sensitive, singly resistant or mixed.

TABLE 5

Resistance study in combination treatment Vs mixed mutant cultures (Optical density at 620 nanometer).

| | | | | | α arteether (A) + nalidixic acid (B) | | | |
|---|---|---|---|---|---|---|---|---|
| | Control | α arteether | | nalidixic acid | | 400 μg/ml A + 50 μg/ml B | 800 μg/ml A + 50 μg/ml B | 400 μg/ml A + 300 μg/ml B | 800 μg/ml A + 300 μg/ml B |
| Bacterial strains | (no compound) | 400 μg/ml | 800 μg/ml | 50 μg/ml | 300 μg/ml | | | | |
| E. coli Wildtype | 0.920 | 0.890 | 0.90 | 0.000 | 0.000 | 0.000 | 0.000 | 0.000 | 0.000 |
| M1 | 0.960 | 0.000 | 0.000 | 0.950 | 0.960 | 0.000 | 0.000 | 0.000 | 0.000 |
| M2 | 0.940 | 0.900 | 0.91 | 0.000 | 0.000 | 0.000 | 0.000 | 0.000 | 0.000 |
| M1 + M2 | 0.930 | 0.920 | 0.930 | 0.910 | 0.920 | 0.000 | 0.000 | 0.000 | 0.000 |

What is claimed is:

1. An anti-microbial composition comprising two components: (a) a quinolone drug that kills bacteria having a gyrase enzyme that is sensitive to said drug; and (b) α-arteether that kills bacteria that are resistant to the quinolone drug by virtue of a mutation in a gyrase gene thereof; the α-arteether and the quinolone drug being present in the composition in respective amounts effective to inhibit development of bacterial resistance to the quinolone drug or α-arteether that would otherwise arise upon contact of a bacterial strain with either of the components singly.

2. A composition as claimed in claim 1, wherein the quinolone drug comprises nalidixic acid.

3. A composition as claimed in claim 1, wherein the ratio of the α-arteether and the quinolone drug in the composition is about 8:1 to 20:1.

4. A composition as claimed in claim 1, wherein the quinolone drug is selected from the group of fluoroquinolones consisting of Ciprofloxacin, Norfloxacin, Levofloxacin, Sparfloxacin, Oxfloxacin and Lomefloxacin.

5. A composition as claimed in claim 2, wherein the concentration of nalidixic acid is at least 50 μg/ml.

6. A composition as claimed in claim 1, wherein the concentration of α-arteether in the composition is about 2 μg to 500 μg/ml.

7. A composition as claimed in claim 1, wherein the concentration of α-arteether in the composition is about 400 μg/ml.

8. A composition as claimed in claim 6, wherein the concentration of the quinolone drug in the composition is about 0.5 mg to 500 mg.

9. A composition as claimed in claim 1 further comprising a solvent.

10. A composition as claimed in claim 9, wherein neutralized sterile vegetable oil is present as the solvent in an amount of at least 1 ml.

11. A composition as claimed in claim 1, wherein the said components are DNA gyrase inhibitors with counter-action properties against resistant mutants of each other.

12. A composition as claimed in claim 1, wherein the quinolone drug is selected from the group consisting of nalidixic acid and oxalinic acid.

13. A composition as claimed in claim 1, wherein the quinolone drug is selected from the group consisting of Lomefloxacin, tosufloxacin and temafloxacin.

14. A method for the development of an anti-microbial composition, said method comprising the step of mixing α-arteether and a quinolone drug in respective amounts effective to inhibit development of bacterial resistance to the anti-microbial composition upon contact of the composition with a bacterial strain having a gyrase enzyme.

15. A method as claimed in claim 14, wherein the ratio of α-arteether to the quinolone drug in the composition is about 8:1 to 20:1.

16. A method as claimed in claim 14, wherein the quinolone drug is nalidixic acid.

17. A method as claimed in claim 14, wherein the quinolone drug is selected from the group of fluoroquinolones consisting of Ciprofloxacin, Norfloxacin, Levofloxacin, Sparfloxacin, Oxfloxacin and Lomefloxacin.

18. A method as claimed in claim 16, wherein the concentration of nalidixic acid in the composition is at least 50 μg/ml.

19. A method as claimed in claim 18, wherein the concentration of α-arteether in the composition is about 2 μg to 50 μg/ml.

20. A method as claimed in claim 18, wherein the concentration of α-arteether in the composition is about 400 μg/ml.

21. A method as claimed in claim 18, wherein the concentration of the quinolone drug in the composition is about 0.5 mg to 500 mg.

22. A method as claimed in claim 14 further comprising including a solvent with the α-arteether and the quinolone drug.

23. A method as claimed in claim 22, wherein the solvent is a neutralized sterile vegetable oil.

24. A method for treating a bacterial infection in a mammal, wherein the bacterial infection comprises bacteria that are sensitive to a quinolone drug or α-arteether, said bacteria having a gyrase gene that can mutate to cause development of bacterial resistance to the quinolone drug or α-arteether in a later generation of the bacteria, said method comprising:

a) providing the composition of claim 1; and
b) administering the composition to the mammal in a therapeutically effective amount with inhibition of the development of the bacterial resistance.

25. A method for treating a bacterial infection in a mammal, wherein the bacterial infection comprises bacteria that are sensitive to a quinolone drug or α-arteether, said bacteria having a gyrase gene that can mutate to cause development of bacterial resistance to the quinolone drug or α-arteether in a later generation of the bacteria, said method comprising:

a) providing the composition of claim 2; and
b) administering the composition to the mammal in a therapeutically effective amount with inhibition of the development of the bacterial resistance.

26. A method for treating a bacterial infection in a mammal, wherein the bacterial infection comprises bacteria that are sensitive to a quinolone drug or α-arteether, said bacteria having a gyrase gene that can mutate to cause development of bacterial resistance to the quinolone drug or α-arteether in a later generation of the bacteria, said method comprising:

a) providing the composition of claim 3; and
b) administering the composition to the mammal in a therapeutically effective amount with inhibition of the development of the bacterial resistance.

27. A method for treating a bacterial infection in a mammal, wherein the bacterial infection comprises bacteria that are sensitive to a quinolone drug or α-arteether, said bacteria having a gyrase gene that can mutate to cause development of bacterial resistance to the quinolone drug or α-arteether in a later generation of the bacteria, said method comprising:

a) providing the composition of claim 6; and
b) administering the composition to the mammal in a therapeutically effective amount with inhibition of the development of the bacterial resistance.

28. A method for treating a bacterial infection in a mammal, wherein the bacterial infection comprises bacteria that are sensitive to a quinolone drug or α-arteether, said bacteria having a gyrase gene that can mutate to cause development of bacterial resistance to the quinolone drug or α-arteether in a later generation of the bacterial, said method comprising administering to the mammal a quinolone drug and α-arteether in respective amounts effective to inhibit the development of the bacterial resistance.

* * * * *